United States Patent [19]

Klaveness et al.

[11] Patent Number: 5,536,490
[45] Date of Patent: Jul. 16, 1996

[54] CONTRAST AGENTS

[75] Inventors: Jo Klaveness; Hanno Priebe, both of Oslo; Pål Rongved, Nesoddtanger, all of Norway; Lars Stubberud, Södertälje, Sweden

[73] Assignee: Nycomed Imaging AS, Oslo, Norway

[21] Appl. No.: 119,217

[22] PCT Filed: Mar. 28, 1992

[86] PCT No.: PCT/EP92/00715

§ 371 Date: Oct. 29, 1993

§ 102(e) Date: Oct. 29, 1993

[87] PCT Pub. No.: WO92/17212

PCT Pub. Date: Oct. 15, 1992

[30] Foreign Application Priority Data

Mar. 28, 1991 [GB] United Kingdom ............... 9106673

[51] Int. Cl.⁶ ..................... A61K 38/00; A61K 49/00
[52] U.S. Cl. ........................... 424/9.52; 424/9.51
[58] Field of Search .................. 424/9, 9.52, 9.51; 128/662.02

[56] References Cited

U.S. PATENT DOCUMENTS

| | | | |
|---|---|---|---|
| 4,265,251 | 5/1981 | Tickner | 424/9 |
| 4,900,540 | 2/1990 | Ryan et al. | 424/9 |
| 5,271,928 | 12/1993 | Schneider et al. | 424/9 |
| 5,362,478 | 11/1994 | Desai et al. | 424/9 |

FOREIGN PATENT DOCUMENTS

| | | |
|---|---|---|
| 3035189 | 8/1989 | Australia . |
| 0327490 | 8/1989 | European Pat. Off. . |
| 0441468 | 8/1991 | European Pat. Off. . |
| 0458745 | 11/1991 | European Pat. Off. . |
| WO-A-9204392 | 3/1992 | WIPO . |

OTHER PUBLICATIONS

Juliano et al., "Interactions of polymerized phospholipid vesicles w/cells. Update, processing, and toxicity in macrophages." Biochim. Biophys. ACTA 812(1985) 42–48.

Juliano, et al., STN File Server, File Biosis, & Biological Abstract, vol. 79, 1985.

*Primary Examiner*—Allen J. Robinson
*Assistant Examiner*—Mary C. Cebulak
*Attorney, Agent, or Firm*—Bacon & Thomas

[57] ABSTRACT

The invention relates to diagnostic ultrasound contrast agents comprising vesicles comprising an amphiphilic phospholipid material capable of formation of gas-containing vesicles wherein the vesicles contain gas which comprises sulphur hexafluoride. The contrast agents and vesicles exhibit good stability in vivo upon administration and may if desired incorporate biodegradable linkages so as to possess particularly desired levels of biodegradability.

40 Claims, No Drawings

CONTRAST AGENTS

This application is a 371 of PCT/EP92/00715 filed Mar. 28, 1992.

This invention relates to novel contrast agents, more particularly to new gas-containing or gas-generating contrast agents of use in diagnostic ultrasonic imaging.

It is well known that ultrasonic imaging comprises a potentially valuable diagnostic tool, for example in studies of the vascular system, particularly in cardiography, and of tissue microvasculature. A variety of contrast agents has been proposed to enhance the acoustic images so obtained, including suspensions of solid particles, emulsified liquid droplets, gas bubbles and encapsulated gases or liquids. It is generally accepted that low density contrast agents which are easily compressible are particularly efficient in terms of the acoustic backscatter they generate, and considerable interest has therefore been shown in the preparation of gas-containing and gas-generating systems.

Initial studies involving free gas bubbles generated in vivo by intracardiac injection of physiologically acceptable substances have demonstrated the potential efficiency of such bubbles as contrast agents in echocardiography; such techniques are severely limited in practice, however, by the short lifetime of the free bubbles. Interest has accordingly been shown in methods of stabilising gas bubbles for echocardiography and other ultrasonic studies, for example using emulsifiers, oils, thickeners or sugars.

WO 80/02365 discloses the use of gelatin-capsulated gas microbubbles for enhancing ultrasonic images. Such microbubbles do not, however, exhibit adequate stability at the dimensions preferred for use in echocardiography (1–10 μm) in view of the extreme thinness of the encapsulating coating.

U.S. Pat. No. 4,774,958 discloses the use of microbubble dispersions stabilised by encapsulation in denatured protein, e.g. human serum albumin. Such systems permit the production of microbubble systems having a size of e.g. 2–5 μm but still do not permit efficient visualisation of the left heart and myocardium.

EP-A-0327490 discloses, inter alia, ultrasonic contrast agents comprising a microparticulate synthetic biodegradable polymer (e.g. a polyester of a hydroxy carbonic acid, a polyalkyl cyanoacrylate, a polyamino acid, a polyamide, a polyacrylated saccharide or a polyorthoester) containing a gas or volatile fluid (i.e. having a boiling point below 60° C.) in free or bonded form. Emulsifiers may be employed as stabilisers in the preparation of such agents, but such emulsifiers do not chemically interact with the polymer.

We have now found that particularly effective ultrasonic contrast agents may be obtained by encapsulating gas bubbles or gas generating systems with polymers containing chemically linked surface active, i.e. amphiphilic, moieties. Thus the surface active properties of the amphiphilic groups stabilise the microbubble system by reducing surface tension at the gas-liquid interfaces, e.g. by forming monolayers or one or more bilayers (alternatively known by the terms micelles, vesicles, liposomes and niosomes) at said interfaces, while the linking of the groups through the polymer system generates further stability. Flexibility of the encapsulating materials also enhances the image density afforded by such contrast agents. For simplicity the terms "vesicle" is used herein to denote all such microbubble structures prior to or after cross-linking or polymerisation. It should be noted that under some conditions irregularly shaped structures may be formed, e.g. microtubules which may join with or even entrap spherical structures.

Thus according to one aspect of the present invention there are provided contrast agents for use in diagnostic ultrasound studies comprising microbubbles of gas or a gas precursor encapsulated by non-proteinaceous crosslinked or polymerised amphiphilic moieties.

The term "crosslinked" is used herein to denote that the amphiphilic moieties are linked to each other to form a polymeric structure which may incorporate one or more polymer systems (including copolymers).

A major advantage of contrast agents according to the invention is that they may be designed to a particular desired level of biodegradability in vivo by selecting appropriate biodegradable linkages at appropriate positions. It will be appreciated that in order to be effective the contrast agents must be stable throughout the ultrasonic examination but are preferably metabolised or removed safely from the circulation system shortly thereafter. Contrast agents in accordance with the invention should thus preferably have a half-life in vivo of not more than 48 hours, for example 1–12 hours.

Biodegradable linkages which may be present in contrast agents according to the invention include amide, imide, imine, ester, anhydride, acetal, carbamate, carbonate, carbonate ester and disulphide groups. At least one such group should preferably be present in the amphiphilic moiety, in the hydrophilic and/or lipophilic portion; it may be advantageous to position the group in the hydrophilic part to facilitate enzymic interaction in vivo. It is further preferred that biodegradable linkages be present in the polymer backbone to ensure substantial breakdown of the polymer in the body.

Any biocompatible gas may be employed in the contrast agents of the invention, for example air, nitrogen, oxygen, hydrogen, nitrous oxide, carbon dioxide, helium, argon, sulphur hexafluoride and low molecular weight optionally fluorinated hydrocarbons such as methane, acetylene or carbon tetrafluoride. The gas may be free within the microbubble, advantageously in the form of a gas-filled "microballoon" since the echogenicity of such products may be enhanced by virtue of their relatively flexible nature. Alternatively the gas may be trapped or entrained within a containing substance. The term "gas" as used herein includes any substances in gaseous form at 37° C.

Gas precursors include carbonates and bicarbonates, e.g. sodium or ammonium bicarbonate and aminomalonate esters. The term "gas precursor" as used herein also embraces substances such as volatile hydrocarbons which may initially be encapsulated but thereafter are partially or completely removed from the vesicles, e.g. by evaporation or freeze-drying, to be replaced by gas.

For applications in echocardiography, in order to permit free passage through the pulmonary system and to achieve resonance with the preferred imaging frequency of about 0.1–15 MHz, it may be convenient to employ microbubbles having an average size of 0.1–10 μm, e.g. 1–7 μm. Substantially larger bubbles, e.g. with average sizes of up to 500 μm, may however be useful in other applications, for example gastrointestinal imaging or investigations of the uterus or Fallopian tubes.

If desired the microbubbles may incorporate particulate stabilisers, for example inorganic materials such as silica or iron oxide which are only partially wetted by the solvent system employed, e.g. having a particle size of 1–500 nm. Colloidal silica having a particle size of 5–50 nm may advantageously be employed for this purpose.

Polymer systems which may be employed in the contrast agents of the invention include carbohydrates such as dextrans and starches, chitin, chitosan, carboxymethylchitosan, alginate, hyaluronic acid, polyacrylamides, polycyanoacrylates, hydroxyalkylpolycyanoacrylates, polyhydroxy acids such as polylactic acids, polyhydroxybutyrates, polyglycolic acids, polylactide-glycolides, polyorthoesters, polyanhydrides, polyurethanes, polyester imides, polyimides, polyacetals, poly-epsilon-caprolactones, polydioxanones, polyaminotriazoles, poly(amideenamines), poly(amide-urethanes), polyphosphazenes, polyvinyl alcohols, organo-polysiloxanes, poly(enolketones) and copolymers of these materials, modified as necessary to introduce hydrophilic or lipophilic moieties.

The contrast agents according to the invention may be prepared by forming a fluid dispersion of vesicles comprising a gas or gas precursor encapsulated by amphiphilic material followed by crosslinking or polymerisation of the amphiphilic material.

The vesicles will normally comprise a substantially spherical monolayer or multilayer of the amphiphilic material. The hydrophilic moieties of the amphiphiles will be physically associated to form a contiguous layer while the lipophilic moieties will also form a layer which may be inside or outside the hydrophilic layer. In bilayers, two layers of the amphiphilic material may be superimposed; thus, for example, a first layer of amphiphilic material may form in which the lipophilic groups are on the outside. A second layer of amphiphilic material may then overlay the first layer with the lipophilic groups adjacent to the lipophilic groups of the first layer and the hydrophilic groups on the outside. Similarly, a bilayer may have the lipophilic groups on the outside and inside and the hydrophilic groups sandwiched between.

Where the fluid in which the vesicles are dispersed is polar, for example aqueous, the hydrophilic groups of the vesicles will tend to be on the outside of the micelles and the lipophilic groups will be on the inside forming a monolayer. On the other hand, if the dispersing fluid is a polar, the lipophilic groups will be on the outside, particularly if the encapsulated material is hydrophilic, e.g. a gas precursor or a solid material containing absorbed or entrained gas, possible in association with a polar liquid. Bilayers may form when the encapsulated material is of the same type, i.e. hydrophilic or lipophilic, as the dispersing fluid.

The amphiphiles used in accordance with the present invention will carry functional groups permitting crosslinking or polymerisation. These may in some instances be groups imparting hydrophilic or lipophilic character or they may be independent of the amphiphilic groupings.

The amphipiles may be considered in three categories:

1. The amphiphiles may carry at least two simple reactive groups such as hydroxyl, amino or carboxyl groups which are capable of reacting with polyvalent reactive monomers or preformed polymers. For example, if the amphiphile carries two hydroxyl groups (in the hydrophilic moiety), a dicarboxylic acid such as suberic acid may be reacted with the vesicles after encapsulation of the gas or gas precursor to provide a crosslinked or polymerised structure. Diaminoamphiphiles may similarly be reacted with dicarboxylic acids while dicarboxylic amphiphiles may be reacted with diamines or diols. Additional crosslinking may be provided by trifunctional reagents. A catalyst will normally be present to assist reaction.

The crosslinking agent may itself be amphiphilic so that the vesicle will form with the lipophilic and hydrophilic groups of the first amphiphile and the amphiphilic crosslinking agent in alignment, whereupon crosslinking between the reactive functional groups may be initiated.

As indicated above, it is particularly advantageous for the polymerised or crosslinked amphiphile to be biodegradable, especially into relatively simple water soluble units. In the case of the ester and amide bonds referred to above, esterase and amidase enzymes will commonly be available in the vascular system and can degrade the encapsulating material back to separate amphiphile molecules and the diamine, diol or diacid reagents which under physiological conditions will not recombine.

If desired, even more biolabile crosslinking groups such as carbonate ester groups may be introduced e.g. using orthoester crosslinking agents. Another useful class of crosslinking agents have the formula (I)

(where Y and Z, which may be the same or different, are —O—, —S— or —NR$^3$—;

$R^1$ and $R^2$, which may be the same or different, are hydrogen atoms or carbon-attached monovalent organic groups or together represent a carbon-attached divalent organic group;

$R^3$ is a hydrogen atom or an organic group; the symbols n, which may be the same or different, are zero or 1;

$R^8$ and $R^9$, which may be the same or different are divalent organic groups, for example alkylene or alkylidene groups having 1–12 carbon atoms; and $A^1$ and $A^2$ are functional groups, for example reactive with hydroxyl, amino or carboxyl groups), since the crosslinking groups so introduced contain units of formula

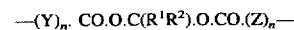

(where Y, Z, each n, $R^1$ and $R^2$ are as defined above) which are particularly readily degraded by common esterases, while exhibiting stability in the absence of enzymes.

$R^1$, $R^2$ and $R^3$ may each be a hydrocarbyl or heterocyclic group, for example having 1–20 carbon atoms, e.g. an alkyl or alkenyl group (preferably having up to 10 carbon atoms), a cycloalkyl group (preferably having up to 10 carbon atoms), an aralkyl group (preferably having up to 20 carbon atoms), an acyl group (preferably having up to 20 carbon atoms) or a heterocyclic group having up to 20 carbon atoms and one or more heteroatoms selected from O,S and N; such a hydrocarbyl or heterocyclic grouping may carry one or more functional groups such as halogen atoms or groups of the formulae —NR$^4$R$^5$, —CONR$^4$R$^5$, —OR$^6$, —SR$^6$ and —COOR$^7$, where $R^4$ and $R^5$ which may be the same or different are hydrogen atoms, acyl groups or hydrocarbyl groups as defined for $R^1$ and $R^2$; $R^6$ is a hydrogen atom or an acyl group or a group as defined for $R^1$ or $R^2$ and $R^7$ is a hydrogen atom or a group as defined for $R^1$ or $R^2$; where $R^1$ and $R^2$ represent a divalent grouping, this may for example be an alkylene or alkenylene group (preferably having up to 10 carbon atoms) which may carry one or more functional groups as defined above. In general $R^1$ and $R^2$ are preferably hydrogen or small groups such as $C_{1-4}$ alkyl groups.

2. The amphiphile may contain polymerisable groupings which can be caused to polymerise after vesicle formation. Such polymerisable groupings may, for example, include unsaturated lipophilic chains, e.g. alkenyl or alkynyl groupings containing up to 50 carbon atoms, for example 10–30 carbon atoms, such as oleyl or linoleyl groups or groups containing diacetylene, acryloyl or methacryloyl groupings. Polymerisation of such groupings will, in general, yield hydrocarbon backbone polymers the backbones of which are not readily biodegradable, although such polymers may be designed so that the backbone residue resulting from biodegradation is water-soluble, e.g. by virtue of the presence of hydrophilic substituents such as carboxyl or hydroxyl groups, to enhance its dispersibility. The chain length of such polymers is in general preferably such that their molecular weight does not exceed 40,000.

Where a greater degree of biodegradability is required, it may be preferable to avoid formation of polymeric hydrocarbon chains which cannot readily be degraded and to effect polymerisation or crosslinking exclusively through biodegradable groups such as ester, carbonate, carbamate, amide or imide bonds of the type referred to above. In general, the functional groups leading to such bonds will be hydrophilic and thus lead to crosslinking between the hydrophilic parts of the amphiphiles.

However, polymerisation of lipophilic hydrocarbon chains may be used to yield a biodegradable polymer if the amphiphile comprises a biodegradable hydrophilic moiety carrying two such chains; where the lipophilic chains of adjacent amphiphile molecules become crosslinked, e.g. via unsaturated carbon-carbon bonds, the extended lipophilic groupings so formed will be separated by the biodegradable hydrophilic groups; on biodegradation, the polymeric structure will thus break up into relatively small lipophilic molecules carrying the residues of the degraded hydrophilic moieties.

3. A soluble amphiphilic polymer carrying appropriate functional groups may be further polymerised or crosslinked after vesicle formation. Such substances include polyamino acids and carbohydrates carrying lipophilic groups, as well as low molecular weight polyesters, polyamides etc carrying appropriate groups providing amphiphilic character. Thus, for example, hydrophilic polymers, such as those listed above, may be provided with lipophilic chains, e.g. $C_{10-30}$ alkyl, alkenyl or alkynyl groups, to provide suitable amphiphiles for use in accordance with the invention. Chemical methods for the attachment of such lipophilic chains include partial esterification of the hydroxyl groups of polyhydroxy acids, salt formation of anionic surfactants on the amino groups of chitosan or covalent derivatisation of such groups, and attachment of hydrophobic groups to carbohydrates or cyclodextrins by way of ester bonds.

The soluble polymer for further polymerisation may also be an amphiphile polymerised or crosslinked in accordance with (1) or (2) above.

Polymerisable or crosslinkable amphiphiles which may be used in accordance with the invention thus include compounds of the general formula (II).

$$[(X)_p(R^{10})_q]B_r \qquad (II)$$

where X is an anionic, cationic or non-ionic hydrophilic moiety;

$R^{10}$ is a lipophilic group;

B is a group capable of polymerisation or cross-linking;

p and q are integers; and r is zero or, when neither X or $R^{10}$ is capable of polymerisation or crosslinking, is an integer.

The groups X and $R^{10}$ may be joined in various ways. Thus, for example, a hydrophilic group X may carry one or several lipophilic groups $R^{10}$ or a lipophilic group $R^{10}$ may carry one or several hydrophilic groups X. One or more hydrophilic groups X may also join separate lipophilic groups $R^{10}$ as long as the amphiphile can adopt a configuration in which the hydrophilic and lipophilic moieties of adjacent molecules are aligned.

Similarly, the group(s) B (where present) may be attached to one or more of the groups X and $R^{10}$.

To provide or enhance biodegradability, one or more biodegradable groupings W may connect the groups X, $R^{10}$ and B.

The group X may, for example, be a quaternary ammonium grouping $-N(R^{11})_3V$ where the groups $R^{11}$ (which may be the same or different) may be, for example, alkyl, aralkyl or aryl groups containing, for example, up to 20 carbon atoms, and V is an anion. It will be appreciated that one or more of the groups $R^{11}$ may be a lipophilic group $R^{10}$.

Other useful hydrophilic groups X include, hydroxyl, carboxylate, amide, phosphate, sulphate and sulphonate groups. Further examples of hydrophilic groups X include:

| | |
|---|---|
| $O.CH_2.CH_2.N^+(CH_3)_3$ | (choline) |
| $O.CH_2.CH_2.N^+H_3$ | (ethanolamine) |
| $O.CH(NH_3^+).COO^-$ | (serine) |
| $O.CH_2.CH(OH).CH_2OH$ | (glycerol) |
| hexoses and pentoses such as inositol. | |

The group $R^{10}$ may, for example, be a saturated or unsaturated, straight or branched hydrocarbon chain, which may contain, for example, 6–50 carbon atoms and may be interrupted by one or more biodegradable groups W and may carry one or more functional groups permitting chains $R^{10}$ on adjacent amphiphiles to crosslink to form a biodegradable group. Useful groups $R^{10}$ include oleyl and linoleyl groups and chains containing diacetylene groupings.

The group(s) B may be, for example, orthoester groups which form carbonate ester linkages with hydroxyl groups, or hydroxyacid groups (or separate hydroxyl and carboxyl groups) which form ester linkages.

It will be appreciated that the hydrophilic group X may comprise a moiety which is not itself directly responsible for hydrophilic properties, as in the case of a group $R^{11}$ of a quaternary ammonium grouping as defined above, which may for example be a lower alkyl group too small to impart lipophilic character; such groups may also form part of the connection between the groups X and $R^{10}$. In other words, there may be transitional regions between groups X and $R^{10}$ which are not strictly either lipophilic or hydrophilic in themselves but can be regarded as part of either X or $R^{10}$.

Thus, in a special case of the amphiphiles of formula (II), the groups X, $R^{10}$ and B may be attached to a preformed polymer which may be regarded as part of X or of $R^{10}$ according to its chemical and physical character. Such a polymer may be a known hydrophilic polymer on to which lipophilic groups (as discussed above) have been attached, or a lipophilic polymer, e.g. a polyolefin, carrying hydrophilic groups. Alternatively, such a polymer may be obtained by partial polymerisation of an amphiphile of formula (II). In all such cases, the preformed polymer should be sufficiently soluble to permit vesicle formation and should be so functionalised as to permit covalent, ionic or coordinate crosslinking to stabilise the vesicles.

Particularly useful monomeric amphiphiles include cyanoacrylate esters carrying lipophilic esterifying groups (which may also have hydrophilic moieties). Thus, for example, U.S. Pat. No. 4,329,332 describes the micellar polymerisation of lower alkyl cyanoacrylates, a technique which may be extendable to the polymerisation of acrylates of the formula $CH_2=C(CN).CO.O.(C_{6-20}$ aliphatic). Similarly, a di-acrylate of the formula $CH_2=CH.CO.O.(CH_2.CH_2.O)_{98}.(CH_2.CH(Me).O)_{67}$.
$(CH_2.CH_2.O)_{98}.CO.CH=CH_2$ has been used by Ping et al (Int. J. Pharm., 61 (1990) 79–84). Corresponding cyanoacrylates may also be used.

Amphiphilic materials of use in accordance with the invention include the following classes of substances derivatised with lipophilic groups:

- lecithin derivatives,
- polyglycerol,
- polyoxyethylene glycol and ethers thereof,
- polyoxyethylene derivatives of steroids,
- glycosides,
- galactosides,
- hydroxyacids or polyhydroxyacids (including carboxylic, phosphonic, sulphonic and sulphinic acids),
- carbohydrates and derivatives thereof,
- aminoalcohols and derivatives thereof,
- cyanoacrylates,
- acrylamides, and
- hydroxyamides.

Polymerisable Amphiphiles

A number of classes of useful polymerisable amphiphiles are listed below:

1. $CH_2(OB_1).CH(OB_2).CH_2.O.PO(O^{31})O(CH_2)_2N^+(CH_3)_3$ where $B_1$ and $B_2$ may be.

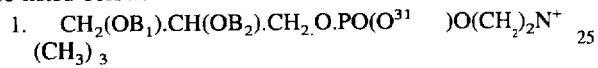

(where n is an integer e.g. 9, 12 or 13) as described in WO 85/04326. Such compounds can be made by conventional phospholipid chemistry as described in Hirth et al (Helv. Chem. Acta 40, 1957, 1928) and Pfeiffer et al (J.Org. Chem. 35, 1970, 221).

Such compounds may thus be prepared by procedures described in EP-A-0032622. The zwitterionic group may be introduced by subjecting the appropriate phosphonic or phosphinic acid or an esterifiable derivative thereof to reaction with glycerol or an esterifiable derivative thereof. The groups $B_1$ and $B_2$ may be introduced into the molecule by esterification using the carboxylic acid of $B_1$ and $B_2$ or an ester-forming derivative thereof. These reactions can be carried out between the glycerol or derivatives thereof on the one hand, and the carboxylic acid and the phosphorus ester on the other, either simultaneously or optionally in steps. Other known methods for the synthesis may equally well be used.

Polymerisation of these compounds may, for example, be obtained by irradiation at 254 nm using a xenon lamp after formation of gas containing liposomes or formation of monolayers of the amphiphiles at the gas/liquid interface.

2. Phospholipids such as phosphodiglycerides and sphingolipids carrying polymerisable groups.

3. Unsaturated oils having hydrophilic groups such as corn oil, sunflower seed oil, soybean oil, safflower oil, peanut oil, cottonseed oil and olive oil.

4. Saturated and unsaturated fatty acid derivatives with hydroxyl groups, for example castor oil and ergot oil which are triglycerides of d-12-hydroxyoleic acid.

5. Compounds as described in "Polymerised Liposomes" (Technical Insights Inc 1988) and Hub et al (J. Macromol.Sci. Chem. A15, (5), 1981,701–715). These may have the structures:

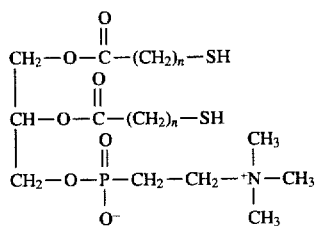

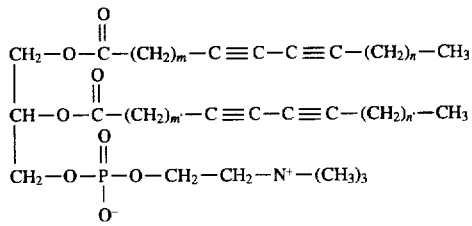

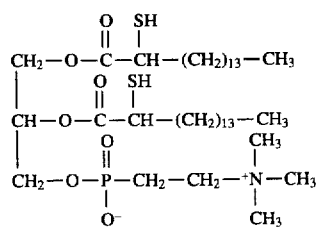

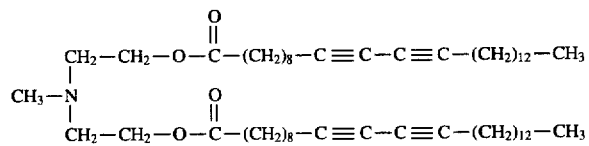

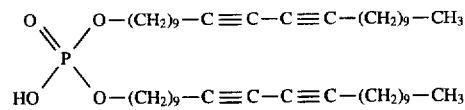

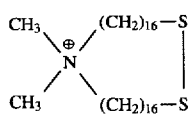

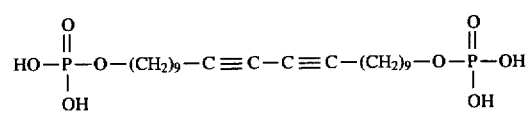

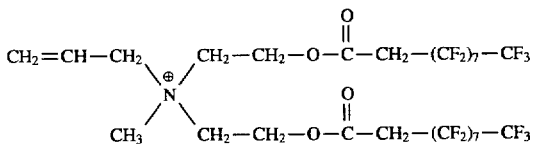

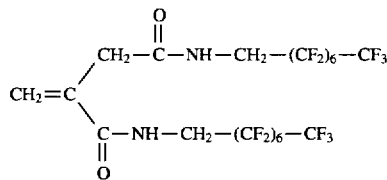

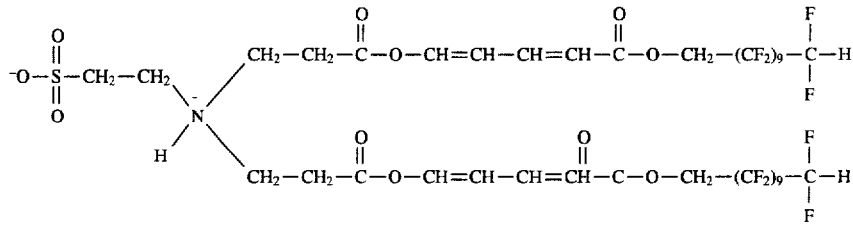

6. Compounds of the formula:
[CH$_3$—(CH$_2$)$_{12}$—C≡C—C≡C—(CH$_2$)$_8$—CO—L—(CH$_2$)$_2$]$_2$M where L and M may be —O—, —S— or —NR$^{12}$ — (where R$^{12}$ is H or an alkyl group), for example the compounds in which L=M=—O—; L=—O—, M=—N(CH$_3$)—; L=—NH—, M=—O—;
L=—O—, M=—N$^+$(CH$_3$)$_2$–Br$^-$ and
L=—O—, M=—N(CH$_2$.CH$_2$.SO$_3$H )—

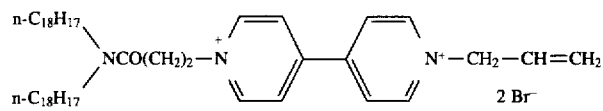

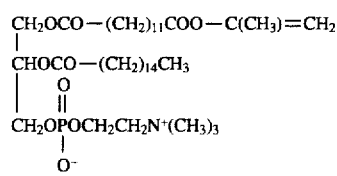

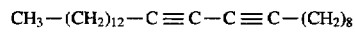

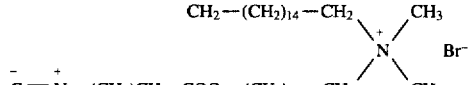

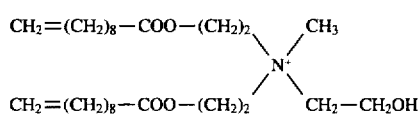

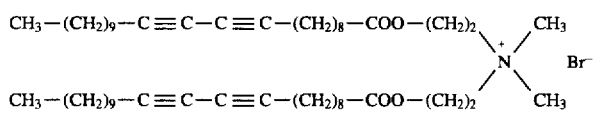

chloride) with the appropriate compound (HLCH$_2$CH$_2$)$_2$M in dry chloroform at 0° C. in the presence of pyridine, if necessary followed by quaternisation.

Synthesis of hexacosane-10,12-diynoic acid is described by Singh et al (Polym. Prep. : Am. Chem. Soc. Div. Polym. Chem; 26 (2), 1985, 184–5). The acid chloride may be prepared by reaction with oxalylchloride.

7. Compounds as described by Paleos (Chem. Soc. Rev. 14, 1985, 45–67), for example of the following structures:

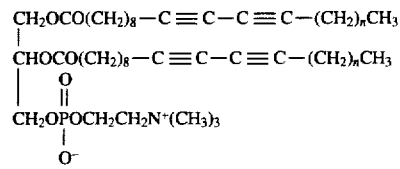

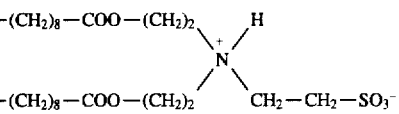

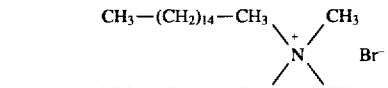

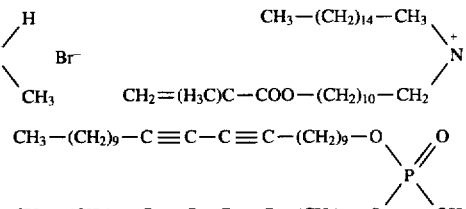

Such compounds may be prepared by reacting a reactive derivative of hexacosane-10,12-diynoic acid (e.g. the acid 8. Esters of α-amino fatty acids which may be self condensed as described by Folda et al (Rapid. Commun. 3, 1982, 167–174) e.g. methyl 2-aminooctadecanoate, docosanyl 2-aminooctadecanoate, methyl 2-aminohexcosanoate and docosanyl 2-amino-hexacosanoate.

These esters of the long chain amino acids may be synthesized from the saturated carboxylic acids by α-bromination using the Hell-Volhard-Zelinsky reaction. The resulting α-bromo acids are converted to the corresponding amino acid by the method of Cheronis et..al (J.Org. Chem. 6 (1949) 349). The methyl esters of the amino acid hydrochlorides are prepared by passing dry HCl-gas through a suspension of the amino acid in refluxing methanol. The docosanyl ester of the amino acid hydrochlorides are synthesized by passing dry HCl-gas through a 1:1 mixture of amino acid and docosanol at 110° C. The ester hydrochlorides are then suspended in dry chloroform and converted to the free amine by passing dry ammonia through the suspension.

9. Long chain esters of sulphosuccinic acid carrying polymerisable functions.
10. Long chain esters of pyridinum dicarboxylic acids (e.g. 3,5-dicarboxy 1-methyl pyridinum iodide) carrying polymerisable functions.
11. Iodinated X-ray contrast agents carrying long chain ether or ester groups having polymerisable functions. Thus, for example, an X-ray contrast agent derived from iothalamic acid may have multiple N-dihydroxyalkyl groups one or two of which may be esterified with long chain fatty acids. Thus, for example, iohexol may be partially protected by forming an acetonide derivative of two of the three dehydroxy alkyl groups, followed by reaction with an activated fatty acid, e.g. the acid chloride, and deprotection to remove the acetonide groups. Such an amphiphile may readily be cross-linked by reaction with a dicarboxylic acid after vesicle formation.
12. Di-fatty acid esters of sorbitan. The multiple free hydroxyl groups which are present permit cross-linking by diacids. Alternatively, the esterifying fatty acid groups may be unsaturated to permit olefinic addition polymerisation.
13. Diesters of the formula
$R^{13}.CO.O.CH(R^{14}).O.CO.R^{13}$ where $R^{14}$ is a hydrophilic group and each $R^{13}$ is a lipophilic group, at least one of $R^{13}$ and $R^{14}$ carrying a polymerisable group and/or functional groups permitting crosslinking. Such compounds may be synthesised by reaction of a dihalide of the formula $R^{14}.CH.Hal_2$ with a salt of an acid $R^{13}.COOH$. They are particularly readily biodegradable.

It may also be beneficial to include in the encapsulating material one or more further amphiphiles such as cholesterol which are not bonded or polymerised but serve to improve the stability and/or flexibility of the microbubbles.

As indicated above the microbubbles may be stabilised by incorporation of particulate material together with the encapsulated gas. Such particles include, for example, silica and iron oxide. The preferred particle size for such stabilising particles is in the range 1 to 500 nm, depending on the size of the microbubbles. The particles should be such that they are only partially wetted by the fluid medium used to disperse the micelles, i.e. the contact angle between the material of the particles and the fluid should be about 90 degrees.

The stabilising particles may carry functional groups which will interact with the amphiphiles to form covalent or other linkages. Particles of the polymerised amphiphiles of formula (II) may be useful in this context. Colloidal silica particles may have a particle size in the range 5–50 nm and may carry silanol groups on the surface which are capable of interaction with the amphiphile by hydrogen bonding or by forming covalent bonds.

The amphiphiles may stabilize the gas or gas precursor by forming a monolayer at the interface between the liquid medium and the gas or gas precursor system, or by forming vesicles consisting of one or more layers containing the gas or gas precursor. The liquid medium may be water or an any non-aqueous liquid with polar, protic, aprotic or a polar characteristics.

The stabilisation of the system by monolayers or multilayers or the formation of the vesicles may be activated, as fully described in the literature, by sonication or even shaking of the amphiphilic material mixture in the appropriate medium, or the vesicles may be formed by any conventional liposome/vesicle-forming principle.

The amphiphiles may form conventional micelles, or inverse micelles when using an apolar non-aqueous medium. The stabilized systems may be dried or freeze-dried or the non-aqueous phase may be evaporated. The resulting dried system may be resuspended in any physiological acceptable solvent such a saline or phosphate buffer, optionally using a suspending or emulsifying agent.

The methods of polymerization used for the stabilisation of the vesicles, are well established methods in polymer chemistry, i.e. as described in "Comprehensive Polymer Science", Vol 1–7, Pergamon Press, Oxford 1989, or "Methoden der Organischen Chemie", Houben-Weyl, Makromolekulare Stoffe Band E20/1-3, Georg Thieme Verlag, Stuttgart 1987. Examples of suitable methods may be chain polymerization methods such as ionic or radical polymerisation or metal catalysed polymerisation, or the systems may polymerize spontaneously by step polymerisation when monolayers or vesicles are formed. Initiators may be UV-irradiation or simple pH-change, or radical initiators. Particularly interesting here may be encapsulation of a substance which, by slight increase in temperature develops a gas, and simultaneously generates free radicals which initiates polymerisation of the surrounding shell. Such a substance is described in "Comprehensive Polymer Science", Vol 3, Pergamon Press, Oxford 1989, p.p. 99, i.e. azo-bis-isobutyronitrile (AIBN), which by UV-irradiation, or by warming to 40° C. starts generating $N_2$ while generating two molecules of cyano-isopropyl radicals which may initiate polymerisation or rapidly pair. Polymerisation of amphiphiles containing unsaturated groupings may also be initiated by sonication (see Price et al., Brit. Polym. J. 23 (1990), 63–66), e.g. when this is used to generate a gas-in-liquid emulsion as described in greater detail hereafter.

A gas entrapped system may be obtained by using a gas precursor or the gas itself may be entrapped. The gas may be entrapped into the amphiphile mixture simply by vigorously shaking the mixture in the presence of air, i.e. creating a gas-in-liquid emulsions as described in U.S. Pat. No. 4684479. Another well established method, described e.g. in U.S. Pat. No. 4,774,958 for creating a gas containing bubble is by sonication of the mixture in the presence of air. Another well known method comprises passing gas through a syringe into a mixture of amphiphile and liquid. As described in U.S. Pat. No. 3,900,420 the microgas-emulsion may be created by using an apparatus for introducing gas rapidly into a fast-flowing liquid. A region of low pressure is created in a liquid containing the amphiphile. The gas is then introduced to the region of low pressure and the gas-in-liquid system is obtained by pumping the liquid through the system.

By using the principle of electrolysis it is possible to generate the gas to be entrapped directly in a container containing the amphiphiles. The electrolytes necessary for the electrolysis may even help to further stabilize the amphiphiles to make the polymerisation possible. An aqueous solution containing electrolytes may generate hydrogen gas at the cathode and oxygen at the anode. The electrodes may be separated by a salt bridge. On adding hydrazine nitrogen gas may be generated at the anode. Using the Kolbe reaction, one may also generate $CO_2$ from carboxylic acids using electrolysis.

As described above, gas entrapped vesicles may be obtained by forming liposomes or vesicles consisting of one or more bilayers. These vesicles may be formed at elevated pressure conditions in such a way that the gas is entrapped in the vesicles.

It is also possible to form a liquid-liquid (e.g. oil-in-water emulsion in the presence of amphiphile systems as discussed above, e.g. by sonication, to form liquid-containing vesicles which can then be polymerised. The polymerised vesicles may then be treated to remove the liquid (conveniently a volatile hydrocarbon) therefrom by evaporation, where the boiling point of the liquid is relatively low, or by extraction with a low-boiling solvent which can itself be removed by evaporation. Evaporation of low-boiling liquid cores may also occur spontaneously during sonication. Where the liquid in the vesicles is water, it can be removed by freeze drying.

The following Examples are given by way of illustration only;

Bis-linoleyl-lecithin is commercially available from Lipids Products, Surrey, UK:

EXAMPLE 1

A saturated solution of the bis-linoleyl-lecithin in an aqueous medium is obtained by mixing 100 mg of the amphiphile in 100 ml of sterile, pyrogen free water. The saturated solution is filtered through a 0.45 µm filter, and the resulting solution is sonicated for 1–10 minutes in the presence of air. During the sonication, air is entrapped into the solution and a gas-in-liquid emulsion is formed. Polymerization of the monolayer of the amphiphile at the gas-liquid interphase is achieved by UV-irradiation of the solution at 254 µm using a xenon lamp, or by addition of a radical initiator.

The resulting product contains microspheres with gas entrapped, i.e., microbubbles. The microbubbles are separated from excess polymerised amphiphiles using a separating funnel. The resulting microbubbbles are resuspended in sterile, pyrogen-free saline, and filled into 10 ml vials. The product is produced using aseptic techniques in a "clean room" (LAF-station) to obtain a sterile, pyrogen free product. The particle sizes of the microspheres are in the range of 0.5–10 µm.

EXAMPLE 2

Example 1 is repeated using as polymerisable amphiphile the compound bis-(trieicoso-10,12-diynoyl) phosphatidyl choline (Hirth et al; Helv Chim Acta 40, 957, 1928).

EXAMPLE 3

100 mg of bis-linoleyl-lecithin are dissolved in a mixture of chloroform/methanol. The mixture is poured into a round bottom flask, and the organic phase is evaporated using a rotavapor in such a way that a thin film of the lecithin derivative is formed at the inner surface of the flask. 10 ml of sterile, pyrogen-free-free water are added and the lipids are dispersed in the solution by sonication at the air/liquid interphase for 5–15 minutes. Gas entrapped vesicles are formed, and the gas-containing microspheres (i.e., microbubbles) are polymerised by UV-irradiation of the solution at 254 nm using a xenon-lamp or by addition of a radical initiator under continuous stirring. Polymerised gas-entrapped vesicles are separated from excess polymerised amphipiles using a separating funnel. The resulting vesicles are suspended in sterile, pyrogen free saline and filtered to obtain a product which contains microbubbles in the range of 0.5–5 µm. The product is produced using aseptic techniques in a "clean room" (LAF-station) to obtain a sterile, pyrogen free product. The final product is filled into 10 ml vials.

EXAMPLE 4

Example 3 is repeated using as polymerisable amphiphile the compound bis-(trieicoso-10,12-diynoyl) phosphatidyl choline (Hirth et al; Helv Chim Acta 40, 957, 1928).

Preparation of polymerisable amphiphiles

EXAMPLE 5

Tetraethylene glycol mono-12-(methacryloyloxy)dodecanoate 12-(Methacryloyloxy)dodecanoic acid (Regen et al., J. Am. Chem. Soc. 1982, 104, 795) (2.75 g, 9.65 mmol) was dissolved in tetrahydrofuran (45 ml) and a solution of oxalyl chloride (2.1 ml, 24.2 mmol) in tetrahydrofuran (5 ml) was added dropwise. The mixture was stirred for 24 hours at room temperature, and then the solvent was evaporated under reduced pressure. The residue was dissolved in tetrahydrofuran (25 ml) and added dropwise to a solution of tetraethylene glycol (1.88 g, 9.65 mmol) and pyridine (0.92 g, 11.7 mmol) in tetrahydrofuran (35 ml). The mixture was stirred for 24 hours at room temperature. The precipitated pyridinium salt was filtered off and the solvent evaporated. Chromatographic purification on a silica gel column (ethyl acetate) afforded 1.67 g (38%) of the title compound. $^1$H NMR (60 MHz, $CDCl_3$): α1.3 (br s, 18H, $(CH_2)_9$), 1.95 (m, 3H, C=$CCH_3$), 2.1–2.6 (m, 2H, $CH_2COO$), 3.5–3.8 (m, 14H, 3×$\underline{CH_2CH_2}$+COO$CH_2\underline{CH_2}$), 4.0–4.4 (m, 4H, $COOCH_2$), 5.52 (m, 1H, vinyl), 6.10 (m, 1H, vinyl).

EXAMPLE 6

Polyethylene glycol (550) methyl ether 12-(methacryloyloxy)dodecanoate 12-(Methacryloyloxy)dodecanoic acid (1.90 g, 6.69 mmol) was dissolved in tetrahydrofuran (20 ml) and a solution of oxalyl chloride (2.12 g, 16.7 mmol) in tetrahydrofuran (10 ml) was added dropwise. The mixture was stirred for 24 hours at room temperature, and then the solvent was evaporated under reduced pressure. The residue was dissolved in tetrahydrofuran (10 ml) and added dropwise to a solution of polyethylene glycol (550) monomethyl ether (3.68 g, 6.69 mmol) and pyridine (0.53 g, 6.69 mmol) in tetrahydrofuran (25 ml). The mixture was stirred for 24 hours at room temperature. The precipitated pyridinium salt was filtered off and the solvent evaporated. Chromatographic purification on a silica gel column (chloroform) afforded 2.31 g (42.3%) of the title compound. 1H NMR (60

MHz, CDCl$_3$): δ1.3 (br s, 18H, (CH$_2$)$_9$), 1.95 (m, 3H, C=CCH$_3$), 2.1–2.5 (m, 2H, CH$_2$COO), 3.11 (s, 3H, CH$_3$O), 3.5–3.8 (m, 25H (average), CH$_2$OC$\underline{H}_2$C$\underline{H}_2$+COOCH$_2$C$\underline{H}_2$, 3.9–4.4 (m, 4H, COOCH$_2$), 5.52 (m, 1H, vinyl), 6.10 (m, 1H, vinyl).

EXAMPLE 7

Polyethylene glycol (2000) methyl ether 12-(methacryloyloxy)dodecanoate 12-(Methacryloyloxy)dodecanoic acid (2.84 g, 0.01 mol) in tetrahydrofuran (20 ml) was reacted with oxalyl chloride (3.0 g, 0.024 mol) to obtain the corresponding acid chloride. This acid chloride (3.0 g, 0.01 mol) dissolved in anhydrous tetrahydrofuran (10 ml) was added dropwise to a mixture of polyethylene glycol (2000) monomethyl ether (20.0 g, 0.01 mol ) and anhydrous pyridine (0.83 g, 0.01 mol) in anhydrous tetrahydrofuran (300 ml). The mixture was stirred for 48 hours at room temperature. The resulting liquid was purified by flash chromatography (silica gel/ethyl acetate) to give 16.5 g (75%) of the title compound. $^1$H NMR (60 MHz, CDCl$_3$): δ1.20 (s, 18H, CH$_2$), 2.15 (m, 2H, C$\underline{H}_2$COOH), 3.5 (s, 3H, CH$_3$O), 3.6 (s, 180H, 90×CH$_2$O), 4.0 (m, 4H, 2×COOC$\underline{H}_2$), 5.7–6.0 (m, 3H, CH$_2$= and =CH).

EXAMPLE 8 a) 16-(Methacryloyloxy)hexadecanoic acid

16-Hydroxyhexadecanoic acid (6.81 g, 25.0 mmol) was dissolved in tetrahydrofuran (150 ml) and the solution was cooled to 0° C. before adding pyridine (2.73 g, 34.5 mmol). Methacryloyl chloride (2.61 g, 25.0 mmol) was dissolved in tetrahydrofuran (75 ml) and added dropwise. The mixture was stirred for 1 hour at 0° C., and then at room temperature for 24 hours. The solvent was removed under reduced pressure (room temperature), the residue suspended in ether (100 ml) and the mixture washed with distilled water. The ether layer was dried (MgSO$_4$) and the ether evaporated. Chromatographic purification on a silica gel column (1:2 ethyl acetate/hexane) afforded 5.0 g (64%) of the title compound. $^1$H NMR (60 MHz, CDCl$_3$): δ1.3 (br s, 26H, (CH$_2$)$_{13}$), 1.95 (m, 3H, C=CCH$_3$), 2.1–2.6 (m, 2H, CH$_2$COO), 4.0–4.4 (m, 2H, COOCH$_2$), 5.52 (m, 1H, vinyl), 6.10 (m, 1H, vinyl).

b) Tetraethylene glycol mono-16-(methacryloyloxy)hexadecanoate 16-(Methacryloyloxy)hexadecanoic acid (2.05 g, 6.57 mmol) was dissolved in tetrahydrofuran (25 ml) and a solution of oxalyl chloride (1.4 ml, 16.5 mmol) in tetrahydrofuran (10 ml) was added dropwise. The mixture was stirred for 24 hours at room temperature, and then the solvent was evaporated under reduced pressure. The residue was dissolved in tetrahydrofuran (10 ml) and added dropwise to a solution of tetraethylene glycol (1.07 g, 5.50 mmol) and pyridine (0.44 g, 5.50 mmol) in tetrahydrofuran (25 ml). The mixture was stirred for 24 hours at room temperature. The precipitated pyridinium salt was filtered off and the solvent evaporated. Chromatographic purification on a silica gel column (2:1 ethyl acetate/hexane) afforded 0.84 g (30%) of the title compound. $^1$H NMR (60 MHz, CDCl$_3$): δ1.3 (br s, 26H, (CH$_2$)$_{13}$), 1.95 (m, 3H, C=CCH$_3$), 2.1–2.6 (m, 2H, CH$_2$COO), 3.5–3.8 (m, 14H, 3×CH$_2$OC$\underline{H}_2$C$\underline{H}_2$+COOCH$_2$C$\underline{H}_2$), 4.0–4.4 (m, 4H, COOCH$_2$), 5.52 (m, 1H, vinyl), 6.10 (m, 1H, vinyl).

EXAMPLE 9

Polyethylene glycol (350) methyl ether 16-(methacryloyloxy)hexadecanoate

The product was prepared from 16-(methacryloyloxy)hexadecanoic acid (prepared as described in Example 8(a)), and polyethylene glycol (350) monomethyl ether using the procedure given in Example 6.

EXAMPLE 10 a) 12-(Acryloyloxy)dodecanoic acid

12-Hydroxydodecanoic acid (5.0 g, 0.023 mol) dissolved in tetrahydrofuran (100 ml) and pyridine (2.16 g, 0,027 mol) was cooled to 0° C. Acryloyl chloride (3.15 g, 0.023 mol) in tetrahydrofuran (75 ml) was then added dropwise to the solution. The mixture was stirred for 5 hours at 0° C. then stirred overnight at room temperature. The precipitated pyridinium salt was filtered off and the solvent removed under vacuum. The resulting liquid was purified by flash chromatography (silica gel/chloroform) to give 2.5 g (40%) of the title compound. $^1$H NMR (60 MHz, CDCl$_3$): δ1.20 (s, 18H, CH$_2$), 2.15 (m, 2H, C$\underline{H}_2$COOH), 4.0 (m, 2H, COOC$\underline{H}_2$), 5.7–6.0 (m, 3H, CH$_2$=and =CH).

b) Tetraethylene glycol mono-12-(acryloyloxy)dodecanoate

12-Acryloyloxydodecanoic acid (2.00 g, 0.007 mol) in diethyl ether (20 ml) was reacted with oxalyl chloride (2.40 g, 0.019 mol) to obtain the corresponding acid chloride. This acid chloride (1.80 g, 0.006 mol) dissolved in anhydrous chloroform (10 ml) was added dropwise to a mixture of tetraethylene glycol (1.20 g, 0.006 mol) and anhydrous pyridine (0.50 g, 0.006 mol) in anhydrous chloroform (30 ml). The mixture was stirred overnight at room temperature. The resulting liquid was purified by flash chromatography (silica gel/ethyl acetate) to give 1.10 g (40%) of the title compound as a colourless oil. $^1$H NMR (60 MHz, CDCl$_3$): δ1.20 (s, 18H, CH$_2$), 2.15 (m, 2H, C$\underline{H}_2$COOH), 3.50 (s, 3H, CH$_3$O), 3.6 (s, 14H, 7×CH$_2$O), 4.0 (m, 5H, 2×COOC$\underline{H}_2$ and OH), 5.7–6.0 (m, 3H, CH$_2$= and =CH).

EXAMPLE 11

Tetraethylene glycol mono-10,12-tricosadiynoate 10,12-Tricosadiynoic acid (2.50 g, 0.007 mol) in tetrahydrofuran (30 ml) was reacted with oxalyl chloride (2.25 g, 0.017 mol) to obtain the corresponding acid chloride. This acid chloride (2.45 g, 0.007 mol) dissolved in anhydrous tetrahydrofuran (10 ml) was added dropwise to a mixture of tetraethylene glycol (1.32 g, 0.007 mol) and anhydrous pyridine (0.83 g, 0.01 mol) in anhydrous tetrahydrofuran (40 ml). The mixture was stirred overnight at room temperature. The precipitated pyridinium salt was filtered off and the solvent removed under vacuum. The resulting liquid was purified by flash chromatography (silica gel/ethyl acetate) to give 1.50 g (41%) of the title compound as a colourless oil. $^1$H NMR (60 MHz, CDCl$_3$): δ0.88 (m, 3H, C$\underline{H}_3$CH$_2$), 1.30 (m, 28H, CH$_2$), 2.20 (m, 6H, CH$_2$), 3.65 (s, 14H, 7×CH$_2$O), 4.20 (m, 2H, CH$_2$CO).

EXAMPLE 12

Polyethylene glycol (550) methyl ether 10,12-tricosadiynoate 10,12-Tricosadiynoic acid (2.50 g, 0.007 mol) in tetrahydrofuran (30 ml) was reacted with oxalyl chloride (2.25 g, 0.017 mol) to obtain the corresponding acid chloride. This acid chloride (2.45 g, 0.007 mol) dissolved in anhydrous tetrahydrofuran (10 ml) was added dropwise to a mixture of polyethylene glycol (550) monomethyl ether (3.85 g, 0.007 mol) and anhydrous pyridine (0.83 g, 0.01 mol) in anhydrous tetrahydrofuran (30 ml). The mixture was stirred overnight at room temperature. The precipitated pyridinium salt was filtered off and the solvent removed under vacuum. The resulting liquid was purified by flash chromatography (silica gel/ethyl acetate) to give 2.72 g (41%) of the title compound as a colourless oil. $^1$H NMR (60 MHz, CDCl$_3$): δ0.88 (m, 3H, C$\underline{H}_3$CH$_2$), 1.30 (m, 28H, CH$_2$), 2.20 (m, 6H, CH$_2$), 3.65 (s, 48H, 24×CH$_2$CO), 3.50 (s, 3H, CH$_3$O), 4.20 (m, 2H, CH$_2$CO).

EXAMPLE 13 a) Methyl 10,12-tricosadiynoate 10,12-Tricosadiynoic acid (3.0 g, 0.0084 mol), methanol (15 ml) and concentrated sulfuric acid (0.8 ml) were heated to reflux and stirred for 1 hour. The cooled mixture was taken up in ether (40 ml) and washed with 10% NaHCO$_3$ (20 ml) and water (20 ml), and the organic phase was dried (MgSO4). Evaporation of the solvent gave 2.68 g (74%) of the title compound. $^1$H NMR (60 MHz, CDCl$_3$): δ0.98 (m, 3H, C$\underline{H}_3$CH$_2$), 1.28 (m, 28H, CH$_2$), 2.25 (m, 6H, CH$_2$), 3.70 (s, 3H, CH$_3$O).

b) N-(2',3'-Dihydroxypropyl)-10,12-tricosadiynamide

Methyl 10,12-tricosadiynoate (1.69 g, 4.67 mmol) was dissolved in methanol. 3-Amino-1,2-propanediol (0.509 g, 5.6 mmol) and sodium methoxide 2.5% solution in methanol (0.146 g, 3 mol %) was added. The mixture was refluxed for 3 hours and the solvent evaporated. The crude product was recrystallized from chloroform. Yield: 1.00 g (51%). $^1$H NMR (60 MHz, CDCl$_3$): δ0.7–1.0 (m, 3H, C$\underline{H}_3$CH$_2$), 1.3 (s, br, 28H, CH$_2$), 2.0–2.4 (m, 6H, CH$_2$), 3.3–3.8 (m, 5H, 2×CH$_2$+CH (propanediol)), 6.0–6.3 (m, 1H, NH).

EXAMPLE 14

N, N'-bis(2,3-dihydroxypropyl)2,4,6-triiodo-5-(tricosa-10.12-diynoylamino) isophthalamide 5-Amino,N,N'-bis(2,3-diacetoxypropyl)-2,4,6-triiodo-isophthalamide (2.19 g, 2.5 mmol) and 10,12-tricosadiynoyl chloride (1.82 g, 5 mmol) were dissolved in 20 ml dichloromethane. The solution was stirred for 3 days at ambient temperature under a nitrogen atmosphere. TLC (ethyl acetate) indicated that the reaction was complete. The reaction mixture was evaporated and dissolved in a mixture of methanol (30 ml) and 1M sodium hydroxide solution (15 ml). After 1 hour TLC (methanol/chloroform) indicated that the reaction was complete. The solution was neutralized with concentrated hydrochloric acid. The residue was dissolved in chloroform and filtered. The solvent was removed and the reaction mixture was purified through silica gel with methanol/chloroform (1:3) to give the title compound. $^1$H NMR (300 MHz, DMSO): δ0.8 (CH$_3$, t), 1.2–1.7 (17×CH$_2$, m), 2.2–2.3 (2×CH$_2$, t), 3.1–3.2 (2×CH$_2$NH, m), 3.3–3.5 (2×CH$_2$OH, m), 3.6–3.8 (2×CHOH), 4.4–4.7 (4×OH, m), 8.4–8.5 (2×CONH, m), 9.8 (2×ArNHCO, s).

EXAMPLE 15

N-(3',4',5'-Trihydroxy-6'-hydroxymethyltetrahydropyran-2'-yl)-10.12-tricosadiynamide 1-Amino-1-deoxy-β-D-galactose (180 mg, 1 mmol), 10,12-tricosadiynoic acid (350 mg, 1 mmol) and 1-ethyl-3-(3-dimethylaminopropyl)carbodiimide were dissolved in 25 ml dry dimethylformamide and stirred at room temperature overnight. The solvent was removed in vacuo, the residue redissolved in chloroform/methanol (1:1), filtered and purified by straight phase chromatography on a CHROMATOTRON. The relevant fractions were collected, concentrated in vacuo, and the product was characterised by NMR.

EXAMPLE 16

6-(2',6'-Diaminohexanoylamino)-3,4,5-trihydroxytetra-hydropyran-2-ylmethy 10,12-tricosadiynoate 1-Amino-1-deoxy-β-D-galactose (180 mg, 1 mmol), and Fmoc-Lys(Boc)-OPfp (650 mg, 1 mmol) were dissolved in 4 ml dry dimethylformamide and stirred at room temperature overnight. The solvent was removed in vacuo, the residue was redissolved in acetonitrile/water (1:1), filtered and purified by reversed phase chromatography (Lobar RP8B, acetonitrile/water 50:50 and 65:35). The relevant fractions were collected, concentrated in vacuo, and the product was characterised by NMR. The purified product (1 g, 1 mmol), 10,12-tricosadiynoic acid (350 mg, 1 mmol) and 1-ethyl-3-(3-dimethylaminopropyl)carbodiimide are dissolved in 10 ml dry dimethylformamide and stirred at room temperature overnight. The solvent is removed in vacuo, the residue redissolved in chloroform/methanol (95:5), filtered and purified by straight phase chromatography on a CHROMATOTRON. The relevant fractions are collected, concentrated in vacuo, and the product is characterised by NMR. The protecting groups of the α-ε amino groups are removed by standard reactions. Boc is removed by treatment with trifluoroacetic acid/methylene chloride for 30 minutes. The solvent is removed in vacuo. Fmoc is removed by treating the residue with 20% piperidine in dimethylformamide for 30 minutes, and the solvent is removed in vacuo. The final product is purified by reversed phase chromatography (Lobar RP8B).

EXAMPLE 17

(3,4,5,6-Tetrahydroxytetrahydropyran-2-ylmethyl) 10,12-tricosadiynoate 1,2;3,4-di-O-isopropylidene-D-galactopyranose (2.6 g, 10 mmol) and 10,12-tricosadiynoic acid (3.5 g, 10 mmol) were dissolved in 25 ml methylene chloride. 1-Ethyl-3(3-dimethylaminopropyl)carbodiimide (2 g, >10 mmol) was added neat. The reaction mixture was stirred overnight at room temperature. The reaction mixture was diluted to 100 ml, extracted with water (2×25 ml), dried over MgSO$_4$ and the solvent was removed in vacuo. The crude product was treated with trifluoroacetic acid (10 ml) at room temperature for 30 minutes, evaporated in vacuo, and purified by straight phase chromatography on a CHROMATOTRON, eluted with methanol/chloroform (5:95). The product was characterised by NMR.

Preparation of ultrasound contrast agents

EXAMPLES 18–41 i) General preparative procedure

The polymerisable amphiphile was dissolved in a minimum of methanol and added to a mixture of water and a hydrocarbon. A comonomer and/or 2,2'-azobisisobutyronitrile (AIBN) dissolved in a minimum of methylene chloride were optionally added and nitrogen was bubbled through the mixture for 1 minute, whereafter the mixture was sonicated under a nitrogen atmosphere using a LABSONIC 2000 apparatus, the sonication probe (length 127 mm, diameter 9.5 mm) being placed 2–3 cm below the surface of the mixture and the energy used being "full scale" or "half scale" in the low position. The resulting emulsions were optionally irradiated with UV light under a nitrogen atmosphere or treated with a redox initiator comprising potassium metabisulphite (0.05 g, 0.22 mmol) in water (1 ml) and potassium peroxosulphate (0.0023 g, $3.3 \times 10^{-3}$ mmol) in water (1 ml). The procedure was modified in Example 31 in that AIBN was added and the mixture was then shaken by hand, whereafter a first portion of comonomer was added and sonication was effected while nitrogen gas was bubbled through the mixture. A further portion of comonomer was then added and the resulting emulsion subjected to UV irradiation.

The specific reaction conditions employed in each Example are set out in Table 1. Similar conditions, e.g. involving sonication for 5 minutes using the full scale setting and irradiating for 1 hour or adding the above-described redox initiator system and stirring carefully for 30 minutes, may be employed to treat the amphiphiles prepared in Examples 14–17.

TABLE 1

| | | Reaction conditions | | | | | | |
|---|---|---|---|---|---|---|---|---|
| Example No | Example in which amphiphile prepared and quantity used (g/mmol) | Volume of water (ml) | Hydrocarbon and volume (ml) | Comonomer and quantity (g/mmol) | Quantity of AIBN (g/mmol) | Sonication level and duration (minutes) | Duration of UV irradiation (hours) | Redox system |
| 18 | 5<br>0.039/0.084 | 50 | PE-5 | MM<br>0.018/0.18 | — | fs-5 | — | — |
| 19 | 5<br>0.037/0.080 | 50 | IP-5 | MM<br>0.018/0.18 | — | hs-3 | — | — |
| 20 | 5<br>0.383/0.83 | 500 | IP-50 | MM<br>0.18/1.8 | 0.20/1.21 | fs-6 | 1.5 | — |
| 21 | 5<br>0.042/0.091 | 50 | IP-5 | MM<br>0.09/0.9 | 0.02/0.12 | fs-3 | 1 | — |
| 22 | 5<br>0.040/0.086 | 50 | PE-2.5 | MM<br>0.018/0.18 | 0.02/0.12 | fs-3 | 1 | — |
| 23 | 6<br>0.053/0.065 | 50 | PE-5 | MM<br>0.018/0.18 | 0.02/0.12 | fs-4 | — | — |
| 24 | 6<br>0.530/0.65 | 500 | PE-50 | MM<br>0.180/1.80 | 0.200/12.0 | fs-8 | 1 | — |
| 25 | 6<br>0.500/0.61 | 500 | PE-50 | MM<br>0.180/1.80 | 0.200/1.20 | fs-8 | 2.5 | — |
| 26 | 6<br>0.200/0.245 | 20 | PE-2 | MM<br>0.018/0.18 | 0.020/0.12 | fs-3 | 1(Ex 26a) | ✓(Ex 26b) |
| 27 | 6<br>0.053/0.065 | 50 | PE-25 | MM<br>0.018/0.18 | 0.020/0.12 | fs-3 | — | ✓ |
| 28 | 6<br>0.054/0.066 | 50 | PE-1 | MM<br>0.018/0.18 | 0.020/0.12 | fs-3 | — | — |
| 29 | 6<br>0.054/0.066 | 50 | TO-5 | MM<br>0.018/0.18 | 0.020/0.12 | fs-3 | — | — |
| 30 | 6<br>0.056/0.069 | 50 | PE-5 | ST<br>0.042/0.41 | 0.020/0.12 | fs-3 | 1 | — |
| 31 | 6<br>0.057/0.070 | 50 | PE-5 | ST<br>0.042/0.41 +<br>0.099/0.95 | 0.020/0.12 | 1 | — | — |
| 32 | 6<br>0.054/0.066 | 50 | IP-5 | — | 0.020/0.12 | fs-6 | — | — |
| 33 | 7<br>0.193/0.090 | 50 | PE-5 | MM<br>0.018/0.18 | 0.02/0.12 | fs-3 | — | — |
| 34 | 8(b)<br>0.042/0.081 | 50 | IP-5 | MM<br>0.018/0.18 | 0.020/0.12 | hs-3 | 1 | — |
| 35 | 8(b)<br>0.046/0.089 | 50 | PE-5 | ST<br>0.042/0.41 | 0.020/0,12 | fs-3 | — | — |
| 36 | 9<br>0.052/0.077 | 50 | PE-5 | — | — | fs-3 | — | — |
| 37 | 10(b)<br>0.036/0.08 | 50 | PE-5 | MM<br>0.018/0.18 | 0.02/0.12 | fs-3 | 1 | — |
| 38 | 11<br>0.047/0.09 | 50 | PE-5 | — | 0.02/0.12 | fs-6 | — | — |
| 39 | 11<br>0.080/0.15 | 50 | PE-5 | — | 0.02/0.12 | fs-3 | 1 | — |
| 40 | 12<br>0.057/0.06 | 50 | PE-5 | — | 0.02/0.12 | fs-3 | — | ✓* |
| 41 | 13(b)<br>0.046/0.11 | 50 | PE-5 | — | 0.02/0.12 | fs-3 | — | — |

KEY - PE = petroleum ether (b.p. 40–60° C.); IP = isopentane; TO = toluene; MM = methylmethacrylate; ST = styrene; fs = full scale; hs = half scale
*Amount of potassium peroxosulphate reduced to 0.002 g (0.003 mmol)

ii) Acoustic characterisation

The acoustic effects of the products of Examples 18–41 were investigated by measuring their ultrasonic transmission as a function of time, over a period of 90 seconds. The tests were performed on samples of emulsified material as formed immediately after sonication and, where appropriate, on the material after subjection to UV irradiation or redox initiation. In the case of Example 25 the sample removed after irradiation was retested after dilution with water (1:1). In the case of EXAMPLE 31 a sample removed after the manual shaking was also tested. A 3.5 MHz broadband transducer was used in a pulse-reflection technique. All the readings were stable during the 90 seconds measurement period, so that a single value (in dB/cm) is sufficient to describe each 90 second measurement. In certain cases the measurements were repeated at time intervals to investigate further the stability of the ultrasound contrast agents. The results are presented in Table 2, the time intervals (in minutes from sonication) to acoustic characterisation are given in brackets for each reading.

TABLE 2

Acoustic characterisations

| Example No. | Acoustic effect after sonication | Acoustic effect after UV irradiation/redox initiation |
|---|---|---|
| 18 | 2.6 (0) | |
| 19 | 3.7 (0) | |
| 20 | 3.7 (0) | 1.4 (90) |
|    | 1.7 (90) | |
| 21 | 0.6 (0) | 0 (60) |
| 22 | 0.7 (0) | 0.5 (60) |
|    | 0.9 (5) | 0 (120) |
| 23 | 5.9 (0) | |
|    | 4.3 (104) | |
| 24 | 6.0 (0) | 4.1 (60) |
| 25 | 4.4 (0) | |
|    | 4.2 (30) | |
|    | 2.9 (150) | 2.9 (150) |
|    |  | 1.4 (150) diluted |
| 26 | 4.0 (0) | 2.8 (20, redox) |
|    | 1.8 60) | 0.4 (60, UV) |
| 27 | 3.6 (0) | 2.9 (10) |
|    | 3.2 (10) | 2.3 (60) |
|    | 3.6 (60) | 0.6 (720) |
| 28 | 0.9 (0) | |
| 29 | 0.6 (0) | |
| 30 | 5.7 (0) | |
|    | 4.1 (60) | 3.2 (60) |
| 31 | 2.5 (after shaking) | |
|    | 5.4 (0) | |
|    | 4.0 (60) | 2.2 (60) |
|    | 3.3 (150) | 1.7 (150) |
| 32 | 4.9 (0) | |
| 33 | 5.5 (0) | |
|    | 4.7 (20) | |
|    | 3.5 (60) | 2.4 (60) |
|    | 3.1 (100) | |
| 34 | 2.2 (0) | 0 (60) |
| 35 | 1.1 (0) | |
| 36 | 2.1 (0) | |
| 37 | 1.7 (0) | 0 (60) |
| 38 | 4.5 (0) | |
| 39 | 5.6 (0) | |
|    | 4.7 (60) | 4.9 (60) |
|    | 4.5 (120) | 4.3 (120) |
| 40 | 3.6 (0) | 0 (60) |
| 41 | 5.3 (0) | | iii) Microscopy analysis

A selection of the products from Examples 18–41 were investigated using a light microscope (Nikin UFX-II) with a micrometer scale. The investigations were generally performed by taking out samples of emulsified material as formed immediately after sonication, except for Example 31 (where the sample was withdrawn after manual shaking), Example 39 (where the sample was withdrawn after UV irradiation) and Example 40 (where samples were withdrawn both immediately after sonication and after redox initiation), and placing each sample between two glass plates. The results of these investigations are presented in Table 3; the time intervals (in minutes from sonication) to microscopy analysis are given for each sample.

TABLE 3

Microscopy analysis

| Example No. | Time after sonication (min) | Size (diam., μm) | Comments (shape, size distribution) |
|---|---|---|---|
| 25 | 10 | 4 | spheres, narrow size distribution |
| 26 | 10 | 10–25 | spheres |
| 27 | 10 | 4 | spheres, narrow size distribution |
| 28 | 10 | 4–6 | spheres, narrow size distribution |
| 29 | 10 | variable | various shapes, broad size distribution |
| 30 | 10 | 4–6 | spheres, narrow size distribution |
| 31 | 10 (after shaking) | 10–100 | large bubbles, unlike the sonicated samples |
| 33 | 10 | 2–3 | spheres |
| 35 | 10 | 10–15 | spheres |
| 36 | 10 | 8–15 | spheres, broad size distribution |
| 38 | 10 | 5–10 | spheres |
| 39 | 10 | 5–10 | spheres, also larger bubbles |
| 40 | 30 | 5–10 | spheres |
| 40 | 30 (after redox) | variable | bubbles of irregular shape |
| 41 | 10 | 4 | spheres, narrow size distribution | iv) Size Exclusion Chromatography

Size Exclusion Chromatrography (SEC) was performed on the freeze dried product from Example 25 using tetrahydrofuran (Rathburn HPLC quality) as eluant and refractive index as detector (Knauer, Germany). The column set used consisted of 3×30 cm columns containing 5 μm styrogel with pore sizes of $10^5$, $10^4$, and 500Å (Polymer Laboratories Ltd., England). Calibration was made against polystyrene standards (Polymer Laboratories Ltd., England). The amphiphilic monomer starting material gave a peak molecular weight of 1,600 Daltons and the polymer product gave a peak molecular weight of 22,000 Daltons, both given in polystyrene equivalents° Using the conversion factor of 0.59 for converting from polystyrene equivalents to "real" molecular weights (the value for PEG given by Dawkins et al., J. Liq. Chromatog. 7, 1739, (1984), these correspond to molecular weights of 944 Daltons for the monomer and 13,000 Daltons for the polymer respectively.

We claim:

1. A diagnostic ultrasound contrast agent comprising stabilized microbubbles of gaseous sulphur hexafluoride encapsulated by non-proteinaceous crosslinked or polymerized amphiphilic moieties.

2. A method of enhancing ultrasound images of a vascular system comprising administering to said system a diagnostic ultrasound contrast agent according to claim 1.

3. Microbubbles comprising an amphiphilic phospholipid material capable of formation of gas-containing microbubbles, said microbubbles containing gas comprising sulphur hexafluoride.

4. Microbubbles as claimed in claim 3 wherein said phospholipid material comprises hydrophilic groups selected from the group consisting of choline, ethanolamine, serine, glycerol, pentoses and hexoses.

5. Microbubbles as claimed in claim 4 wherein said phospholipid material comprises a lecithin or derivative thereof.

6. An aqueous dispersion comprising microbubbles as claimed in claim 3.

7. An aqueous dispersion comprising microbubbles as claimed in claim 4.

8. An aqueous dispersion comprising microbubbles as claimed in claim 5.

9. Microbubbles as claimed in claim 3 wherein said phospholipid material is crosslinked or polymerized.

10. Microbubbles as claimed in claim 9 wherein said crosslinked or polymerized phospholipid material contains biodegradable linkages selected from the group consisting of amide, imide, imine, ester, anhydride, acetal, carbamate, carbonate, carbonate ester and disulphide groups.

11. Microbubbles as claimed in claim 10 wherein said crosslinked or polymerized phospholipid material contains biodegradable amide linkages.

12. Microbubbles as claimed in claim 10 wherein said phospholipid material contains biodegradable crosslinking groups.

13. Microbubbles as claimed in claim 12 wherein said biodegradable crosslinking groups include units of formula

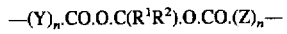

$$-(Y)_n.CO.O.C(R^1R^2).O.CO.(Z)_n-$$

where Y and Z, which may be the same or different, are —O—, —S— or —NR$^3$—; R$^1$ and R$^2$, which may be the same or different, are hydrogen atoms or carbon-attached monovalent organic groups or together represent a carbon-attached divalent organic group; R$^3$ is a hydrogen atom or an organic group; and the symbols n, which may be the same or different, are zero or 1.

14. Microbubbles as claimed in claim 9 obtained from polymerizable phospholipid material containing unsaturated lipophilic chains.

15. Microbubbles as claimed in claim 14 wherein said unsaturated lipophilic chains are oleyl or linoleyl groups or contain diacetylene groupings or acryloyl or methacryloyl groupings.

16. Microbubbles as claimed in claim 9 which are crosslinked between the hydrophilic parts of the phospholipid moieties.

17. Microbubbles as claimed in claim 3 which comprise sulphur hexafluoride stabilized by monolayers of said phospholipid material.

18. Microbubbles as claimed in claim 9 which comprise sulphur hexafluoride stabilized by monolayers of said crosslinked or polymerized phospholipid material.

19. Microbubbles as claimed in claim 3 having an average size of 0.1–10 μm.

20. Microbubbles as claimed in claim 19 having an average size of 1–7 μm.

21. Microbubbles as claimed in claim 9 having an average size of 0.1–10 μm.

22. Microbubbles as claimed in claim 21 having an average size of 1–7 μm.

23. Microbubbles as claimed in claim 9 wherein the crosslinked or polymerized phospholipid material comprises phospholipid material reacted with preformed polymer.

24. An aqueous dispersion comprising microbubbles as claimed in claim 9.

25. A diagnostic ultrasound contrast agent comprising microbubbles as claimed in claim 9.

26. A contrast agent as claimed in claim 25 having a half-life in vivo of 1 to 48 hours.

27. A contrast agent as claimed in claim 26 having a half-life in vivo of 1 to 12 hours.

28. A contrast agent as claimed in claim 25 wherein said microbubbles are dispersed in an aqueous carrier.

29. A process for the preparation of a contrast agent which comprises generating microbubbles comprising amphiphilic phospholipid material capable of formation of gas-containing microbubbles, said microbubbles containing gas comprising sulphur hexafluoride.

30. A process as claimed in claim 29 which comprises shaking or sonicating an amphiphilie-containing mixture comprising a phospholipid in the presence of sulphur hexafluoride to generate a fluid dispersion of said microbubbles.

31. A process as claimed in claim 30 wherein an aqueous amphiphile-containing mixture comprising a phospholipid is used to generate an aqueous dispersion of microbubbles.

32. A process as claimed in claim 30 wherein the contrast agent is isolated by freeze drying.

33. A process for the preparation of a contrast agent which comprises crosslinking or polymerizing microbubbles comprising amphiphilic phospholipid material capable of formation of gas-containing microbubbles, said microbubbles containing gas comprising sulphur hexafluoride.

34. A process as claimed in claim 33 wherein crosslinking or polymerization is effected between the hydrophilic parts of the phospholipid material.

35. A process as claimed in claim 33 wherein crosslinking or polymerization is effected by self condensation of the phospholipid material.

36. A process as claimed in claim 33 wherein the phospholipid material is reacted with a preformed polymer.

37. A process as claimed in claim 33 wherein the contrast agent is isolated by freeze drying.

38. A contrast agent prepared by the process of claim 29.

39. A method of enhancing ultrasound images of a vascular system comprising administering to said system a diagnostic ultrasound contrast agent according to claim 25.

40. A method of enhancing ultrasound images of a vascular system comprising administering to said system a diagnostic ultrasound contrast agent according to claim 38.

* * * * *

UNITED STATES PATENT AND TRADEMARK OFFICE
CERTIFICATE OF CORRECTION

PATENT NO. : 5,536,490
DATED : July 16, 1996
INVENTOR(S) : Jo KLAVENESS et al.

It is certified that error appears in the above-indentified patent and that said Letters Patent is hereby corrected as shown below:

Column 7, line 24, delete "$(O^{31}\ )$" and insert --$(O^-)$--.

Signed and Sealed this

Third Day of December, 1996

Attest:

BRUCE LEHMAN

*Attesting Officer*       *Commissioner of Patents and Trademarks*